(12) United States Patent
Aggarwal et al.

(10) Patent No.: US 10,956,821 B2
(45) Date of Patent: Mar. 23, 2021

(54) ACCURATE TEMPORAL EVENT PREDICTIVE MODELING

(71) Applicant: INTERNATIONAL BUSINESS MACHINES CORPORATION, Armonk, NY (US)

(72) Inventors: Charu C. Aggarwal, Yorktown Heights, NY (US); Lingtao Cao, Hayward, CA (US); Tan Hung M. Ng, San Jose, CA (US); Saket Sathe, Mohegan Lake, NY (US); Deepak S. Turaga, Elmsford, NY (US)

(73) Assignee: International Business Machines Corporation, Armonk, NY (US)

( * ) Notice: Subject to any disclaimer, the term of this patent is extended or adjusted under 35 U.S.C. 154(b) by 722 days.

(21) Appl. No.: 15/363,723

(22) Filed: Nov. 29, 2016

(65) Prior Publication Data

US 2018/0150757 A1    May 31, 2018

(51) Int. Cl.
| | |
|---|---|
| *G06N 20/00* | (2019.01) |
| *G16H 10/60* | (2018.01) |
| *G06N 5/02* | (2006.01) |
| *G16H 50/70* | (2018.01) |
| *G16H 40/63* | (2018.01) |
| *G16H 40/67* | (2018.01) |
| *G16H 50/20* | (2018.01) |
| *G16H 50/50* | (2018.01) |

(52) U.S. Cl.
CPC .............. *G06N 5/02* (2013.01); *G06N 20/00* (2019.01); *G16H 10/60* (2018.01); *G16H 40/63* (2018.01); *G16H 40/67* (2018.01); *G16H 50/20* (2018.01); *G16H 50/50* (2018.01); *G16H 50/70* (2018.01)

(58) Field of Classification Search
CPC ........ G06N 20/00; G06N 20/10; G06N 20/20; G16H 50/70
See application file for complete search history.

(56) References Cited

U.S. PATENT DOCUMENTS

| | | |
|---|---|---|
| 6,272,480 B1 | 8/2001 | Tresp et al. |
| 6,923,763 B1 | 8/2005 | Kovatchev et al. |
| 7,233,936 B1 | 6/2007 | Muller et al. |
| 8,386,401 B2 | 2/2013 | Virkar et al. |
| 8,758,245 B2 | 6/2014 | Ray et al. |
| 9,750,877 B2 * | 9/2017 | Kovelman .......... A61M 5/1723 |
| 2002/0106709 A1 | 8/2002 | Potts et al. |
| 2003/0208113 A1 | 11/2003 | Mault et al. |

(Continued)

FOREIGN PATENT DOCUMENTS

WO    2005110029 A2    11/2005

OTHER PUBLICATIONS

Sudharsan et al., "Hypoglycemia Prediction Using Machine Learning Models for Patients With Type 2 Diabetes," Journal of Diabetes Science and Technology 2015, vol. 9(1), 2015 (5 pages).

(Continued)

*Primary Examiner* — Li Wu Chang
(74) *Attorney, Agent, or Firm* — Robert J. Shatto

(57) ABSTRACT

Embodiments for accurate temporal event predictive modeling by a processor. An average reverse event delay may be determined from one or more event delays in a time-series window. A time-series event may be predicted by applying the average reverse event delay in conjunction with one or more weighted factors in a predictive model.

15 Claims, 9 Drawing Sheets

(56) References Cited

U.S. PATENT DOCUMENTS

| | | | |
|---|---|---|---|
| 2007/0128682 A1* | 6/2007 | Rosman | G16H 50/50 435/14 |
| 2008/0208026 A1 | 8/2008 | Noujaim et al. | |
| 2008/0208072 A1* | 8/2008 | Fadem | A61B 5/0484 600/544 |
| 2009/0177103 A1 | 7/2009 | Bharmi | |
| 2010/0280882 A1* | 11/2010 | Faith | G06Q 10/06375 705/7.37 |
| 2012/0165638 A1 | 6/2012 | Duke et al. | |
| 2013/0238533 A1 | 9/2013 | Virkar et al. | |
| 2013/0338629 A1* | 12/2013 | Agrawal | A61M 5/1723 604/504 |
| 2014/0012511 A1 | 1/2014 | Mensinger et al. | |
| 2014/0187887 A1 | 7/2014 | Dunn et al. | |
| 2014/0309511 A1 | 10/2014 | Stal | |
| 2015/0012472 A1 | 1/2015 | Liang et al. | |
| 2016/0171380 A1* | 6/2016 | Kennel | G06N 7/005 706/12 |
| 2016/0371585 A1* | 12/2016 | McElhinney | G06F 17/5009 |

OTHER PUBLICATIONS

Eljil, "Predicting Hypoglycemia in Diabetic Patients Using Machine Learning Techniques," DSpace, Jun. 2014 (92 pages).

Plis et al., "A Machine Learning Approach to Predicting Blood Glucose Levels for Diabetes Management," Modern Artificial Intelligence for Health Analytics: Papers from the AAAI-14, 2014 (5 pages).

Cameron et al., "Statistical Hypoglycemia Prediction," Journal of Diabetes Science and Technology, vol. 2, Issue 4, Jul. 2008 (10 pages).

Aggarwal et al., "Accurate Temporal Event Predictive Modeling," U.S. Appl. No. 16/587,205, filed Sep. 30, 2019.

Aggarwal et al., "Accurate Temporal Event Predictive Modeling," U.S. Appl. No. 16/587,232, filed Sep. 30, 2019.

List of IBM Patents or Patent Applications Treated as Related, Sep. 26, 2019, 2 pgs.

Mell et al., "The NIST Definition of Cloud Computing," Recommendations of the National Institute of Standards and Technology, U.S. Department of Commerce, Special Publication 800-145, Sep. 2011, 7 pgs.

* cited by examiner

Reverse hypo delay (RHD) and hypoglycemia prediction results

| GroupID | 2hr | | 3hr | | 4hr | |
|---|---|---|---|---|---|---|
| | 10K (without RHD) | 10K (with RHD) | 10K (without RHD) | 10K (with RHD) | 10K (without RHD) | 10K (with RHD) |
| 1 | 83.4 | 89.7 | 78.5 | 86.2 | 76.4 | 82.7 |
| 2 | 83.7 | 88.0 | 79.1 | 84.0 | 77.0 | 81.2 |
| 3 | 84.4 | 89.3 | 79.6 | 85.1 | 77.0 | 82.2 |
| 4 | 84.6 | 88.1 | 80.3 | 84.1 | 78.0 | 81.5 |
| 5 | 83.3 | 88.0 | 78.4 | 83.9 | 76.6 | 81.6 |
| 6 | 82.5 | 86.9 | 78.0 | 82.8 | 76.3 | 80.5 |
| 7 | 84.1 | 89.3 | 79.2 | 85.1 | 76.9 | 82.3 |
| 8 | 83.2 | 88.2 | 78.4 | 84.1 | 77.4 | 81.7 |
| 9 | 83.4 | 88.4 | 79.4 | 84.9 | 76.6 | 82.3 |
| 10 | 83.2 | 87.3 | 78.6 | 83.7 | 77.0 | 81.2 |
| Min | 82.5 | 86.9 | 78.0 | 82.8 | 76.3 | 80.5 |
| Max | 84.6 | 89.7 | 80.3 | 86.2 | 78.0 | 82.7 |
| Mean | 83.6 | 88.3 | 79.0 | 84.4 | 76.92 | 81.7 |

ACCURATE TEMPORAL EVENT PREDICTIVE MODELING

BACKGROUND OF THE INVENTION

Field of the Invention

The present invention relates in general to computing systems, and more particularly to, various embodiments for accurate temporal event predictive modeling by a processor.

Description of the Related Art

In today's society, various medical advances, coupled with advances in technology have made possible a wide variety of attendant benefits, such as the computerized monitoring of a patient, or the storing or organization of data representative of a patient's health records. As computers, processors, storage devices and mobile computing platforms proliferate throughout aspects of society, additional opportunities continue to present themselves for leveraging technology in health care for the benefit of patients, health professionals, and others.

SUMMARY OF THE INVENTION

Various embodiments for accurate temporal event predictive modeling by a processor, are provided. In one embodiment, by way of example only, a method for accurate temporal event predictive modeling by a processor is provided. An average reverse event delay may be determined from one or more event delays in a time-series window. A time-series event may be predicted by applying the average reverse event delay in conjunction with one or more weighted factors in a predictive model.

BRIEF DESCRIPTION OF THE DRAWINGS

In order that the advantages of the invention will be readily understood, a more particular description of the invention briefly described above will be rendered by reference to specific embodiments that are illustrated in the appended drawings. Understanding that these drawings depict only typical embodiments of the invention and are not therefore to be considered to be limiting of its scope, the invention will be described and explained with additional specificity and detail through the use of the accompanying drawings, in which:

FIGS. 7A-B is a diagram of prediction results using average reverse event delay in predictive modeling in accordance with aspects of the present invention;

DETAILED DESCRIPTION OF THE DRAWINGS

Figure 1:
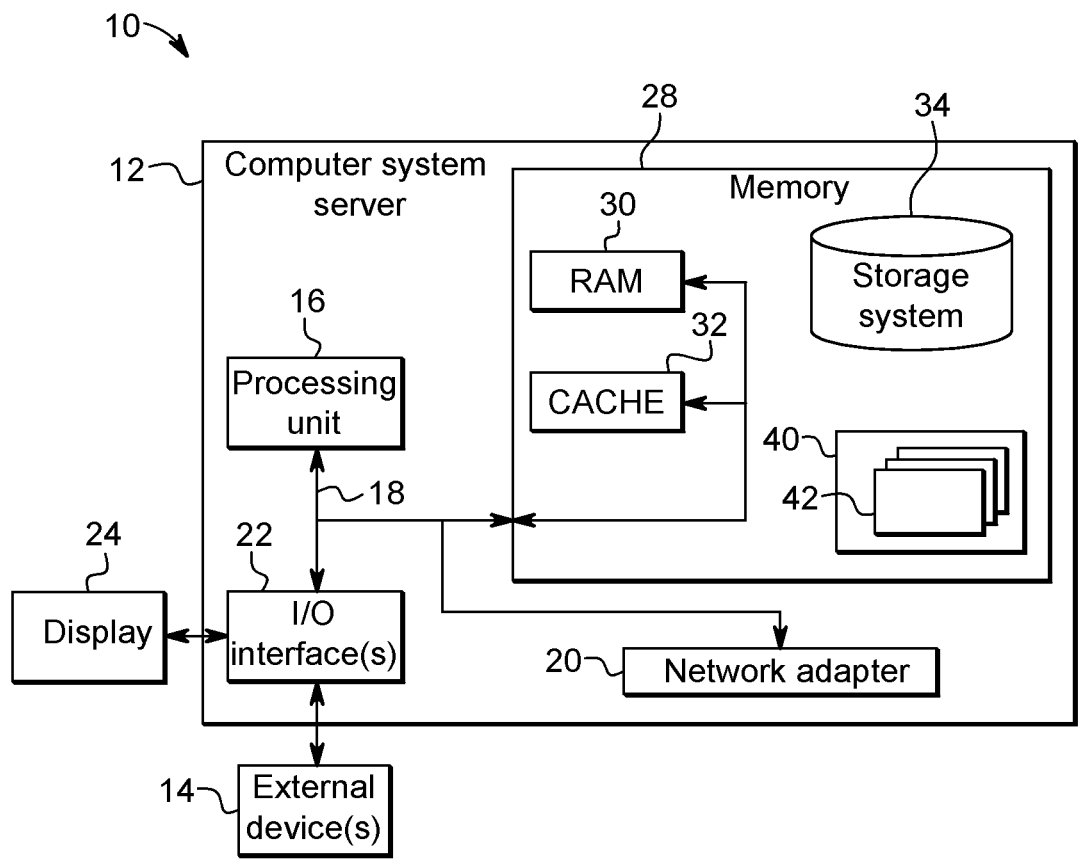
FIG. 1 is a block diagram depicting an exemplary computing node according to an embodiment of the present invention.

Many patients suffer from various diseases, such as diabetes mellitus ("diabetes") that require consistent management and attention. Diabetes is due to either the pancreas not producing enough insulin or the cells of the body not responding properly to the insulin produced. Management of diabetes concentrates on keeping blood sugar levels as close to normal, without causing low blood glucose/sugar ("Hypoglycemia"). Frequently, in order to avoid hypoglycemia, diabetics maintain abnormally high blood glucose levels to provide a "buffer" against low blood glucose levels. This constant high blood glucose level is the root cause of most long-term complications of diabetes, namely, retinopathy, neuropathy, nephropathy, and cardiovascular disease. For example, blood sugar monitoring devices are presently available to provide real-time continuous blood sugar monitoring that alarms the patient upon detection of a hypoglycemia condition. However, there is a need for a computing system to accurately predict a hypoglycemia condition prior to the detection of a hypoglycemia condition in a patient.

In one aspect, the mechanisms of the illustrated embodiments employ artificial intelligence, such as machine learning, to allow computers to simulate human intelligence and choices based on significant amounts of empirical data. Machine learning may capture characteristics of interest, such as the diabetes, and their underlying probability distribution, and a training data set may be used to train a machine learning model. A model or rule set may be built and used to predict a result based on the values of a number of features. The machine learning may use a data set that typically includes, for each record, a value for each of a set of features, and a result. From this data set, a model or rule set for predicting the result is developed.

More specifically, various embodiments are provided for accurate temporal event predictive modeling to predict the occurrence or non-occurrence of an event in a selected time-window. For example, the prediction model will determine whether a patient will experience hypoglycemia after a bolus event in a time-window such as, for example, 3 hours. The hypoglycemia event may be a time-series event that is defined as an event when a time-series value falls below or rises above a selected threshold. For example, in the hypoglycemia prediction scenario, if the sensor glucose (SG) value falls below a threshold, such as for example 70 milligrams per deciliter (mg/dL), then a hypoglycemic event is triggered. In one aspect, the threshold may be a threshold value from a range of desired glucose levels from 70 mg/dL to 140 mg/dL.

The mechanisms of the illustrated embodiments, as will be further described, take a proactive approach to construct accurate predictors for a time-series event prediction problem that involves situations where classes or features are heavily unbalanced, with a rare class or feature being identified as the most important class or feature (or a highest ranked class or feature that is also the most rare), and it is extremely difficult to create predictive models which learn different modes/characteristics of the important rare class. Thus, in one aspect, the present invention provides for a reliable and accurate model for hypoglycemia prediction for diabetes patients.

In an additional aspect, various embodiments are provided for predicting hypoglycemic events in diabetic patients, wherein the hypoglycemic event is defined as blood glucose level dropping below a threshold in time-series window after a bolus is administered by the patient. In one aspect, as used herein, a time-series window may be a selected time period (e.g., a fixed period of time such as 2-4 hours) or a window that includes a selected number of events (e.g., occurrence of at least 2 events). An average event delay and a reverse event delay in a time-series window may be determined. The average event delay may be defined as the average delay from a start of the time-series window after which the bolus event occurs. The average reverse event delay may be defined as the average time from the end of the time-series window before which the event occurs. One or more classifiers may be learned or trained using the average event delay and/or the average event delay in addition to other features. A hypoglycemic event may be predicted in diabetic patients based on learned or trained classifiers.

Additional aspects of the present invention and attendant benefits will be further described, following.

It is understood in advance that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Referring now to FIG. 1, a schematic of an example of a cloud computing node is shown. Cloud computing node 10 is only one example of a suitable cloud computing node and is not intended to suggest any limitation as to the scope of use or functionality of embodiments of the invention described herein. Regardless, cloud computing node 10 is capable of being implemented and/or performing any of the functionality set forth hereinabove.

In cloud computing node 10 there is a computer system/server 12, which is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 1, computer system/server 12 in cloud computing node 10 is shown in the form of a general-purpose computing device. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, system memory 28 may include at least one program product having a set (e.g., at least one) of program modules that are configured to carry out the functions of embodiments of the invention.

Program/utility 40, having a set (at least one) of program modules 42, may be stored in system memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein.

Computer system/server 12 may also communicate with one or more external devices 14 such as a keyboard, a pointing device, a display 24, etc.; one or more devices that enable a user to interact with computer system/server 12; and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, external disk drive arrays, RAID systems, tape drives, and data archival storage systems, etc.

In the context of the present invention, and as one of skill in the art will appreciate, various components depicted in FIG. 1 may be located in a moving vehicle. For example, some of the processing and data storage capabilities associated with mechanisms of the illustrated embodiments may take place locally via local processing components, while the same components are connected via a network to remotely located, distributed computing data processing and storage components to accomplish various purposes of the present invention. Again, as will be appreciated by one of ordinary skill in the art, the present illustration is intended to convey only a subset of what may be an entire connected network of distributed computing components that accomplish various inventive aspects collectively.

Figure 2:
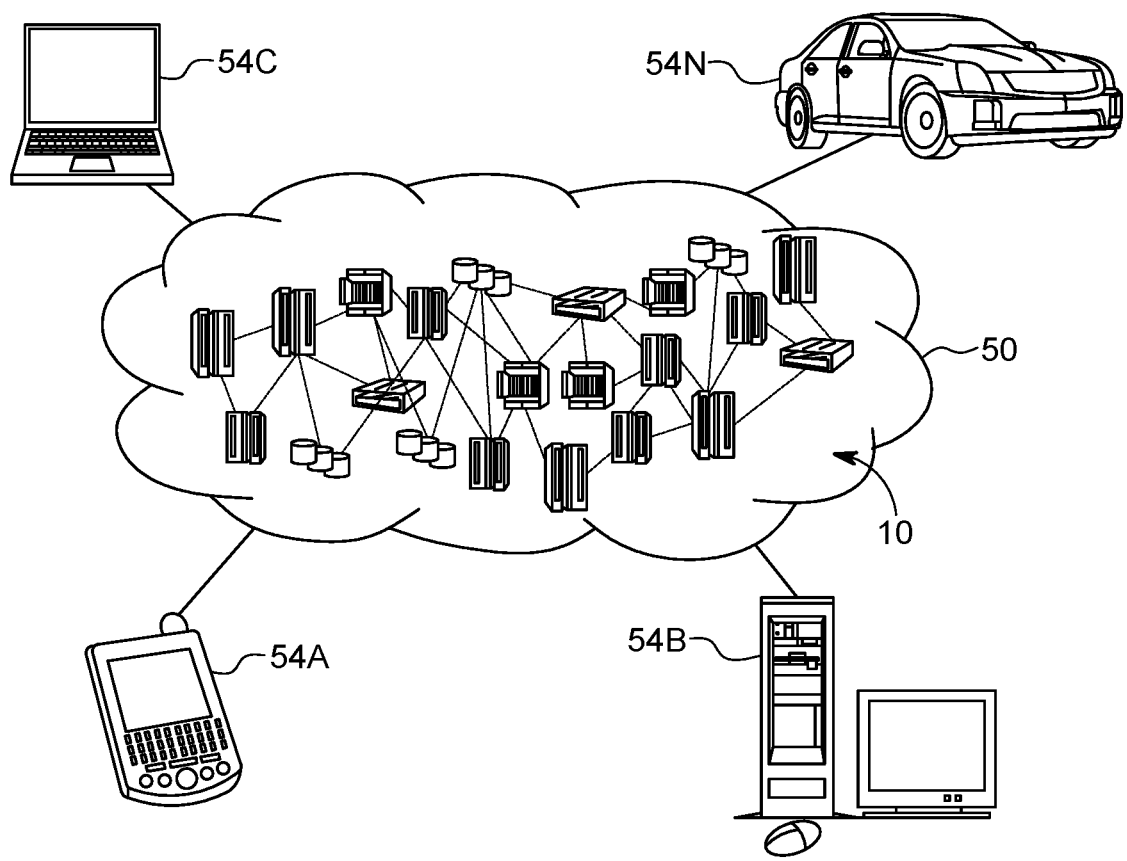
FIG. 2 is an additional block diagram depicting an exemplary cloud computing environment according to an embodiment of the present invention.

Referring now to FIG. 2, illustrative cloud computing environment 50 is depicted. As shown, cloud computing environment 50 comprises one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 2 are intended to be illustrative only and that computing nodes 10 and cloud computing environment 50 can communicate with any type of computerized device over any type of network and/or network addressable connection (e.g., using a web browser).

Figure 3:
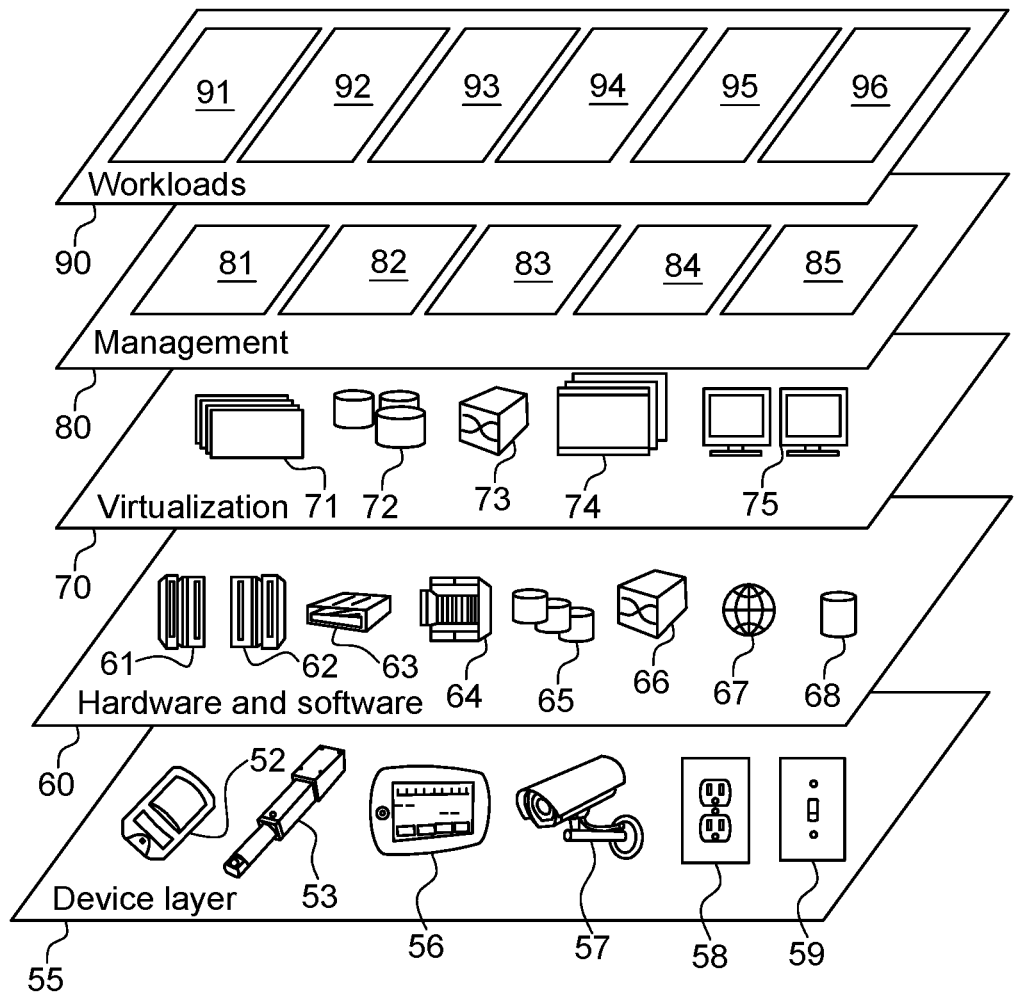
FIG. 3 is an additional block diagram depicting abstraction model layers according to an embodiment of the present invention.

Referring now to FIG. 3, a set of functional abstraction layers provided by cloud computing environment 50 (FIG. 2) is shown. It should be understood in advance that the components, layers, and functions shown in FIG. 3 are intended to be illustrative only and embodiments of the invention are not limited thereto. As depicted, the following layers and corresponding functions are provided:

Device layer 55 includes physical and/or virtual devices, embedded with and/or standalone electronics, sensors, actuators, and other objects to perform various tasks in a cloud computing environment 50. Each of the devices in the device layer 55 incorporates networking capability to other functional abstraction layers such that information obtained from the devices may be provided thereto, and/or information from the other abstraction layers may be provided to the devices. In one embodiment, the various devices inclusive of the device layer 55 may incorporate a network of entities collectively known as the "internet of things" (IoT). Such a network of entities allows for intercommunication, collection, and dissemination of data to accomplish a great variety of purposes, as one of ordinary skill in the art will appreciate.

Device layer 55 as shown includes sensor 52, actuator 53, "learning" thermostat 56 with integrated processing, sensor, and networking electronics, camera 57, controllable household outlet/receptacle 58, and controllable electrical switch 59 as shown. Other possible devices may include, but are not limited to various additional sensor devices, networking devices, electronics devices (such as a remote control device), additional actuator devices, so called "smart" appliances such as a refrigerator or washer/dryer, and a wide variety of other possible interconnected objects.

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provides cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provides pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and, in the context of the illustrated embodiments of the present invention, various accurate temporal event predictive modeling workloads and functions 96. In addition, accurate temporal event predictive modeling workloads and functions 96 may include such operations as data analysis (including data collection and processing from various environmental sensors), and predictive data analytics functions. One of ordinary skill in the art will appreciate that the accurate temporal event predictive modeling workloads and functions 96 may also work in conjunction with other portions of the various abstractions layers, such as those in hardware and software 60, virtualization 70, management 80, and other workloads 90 (such as data analytics processing 94, for example) to accomplish the various purposes of the illustrated embodiments of the present invention.

Figure 4:
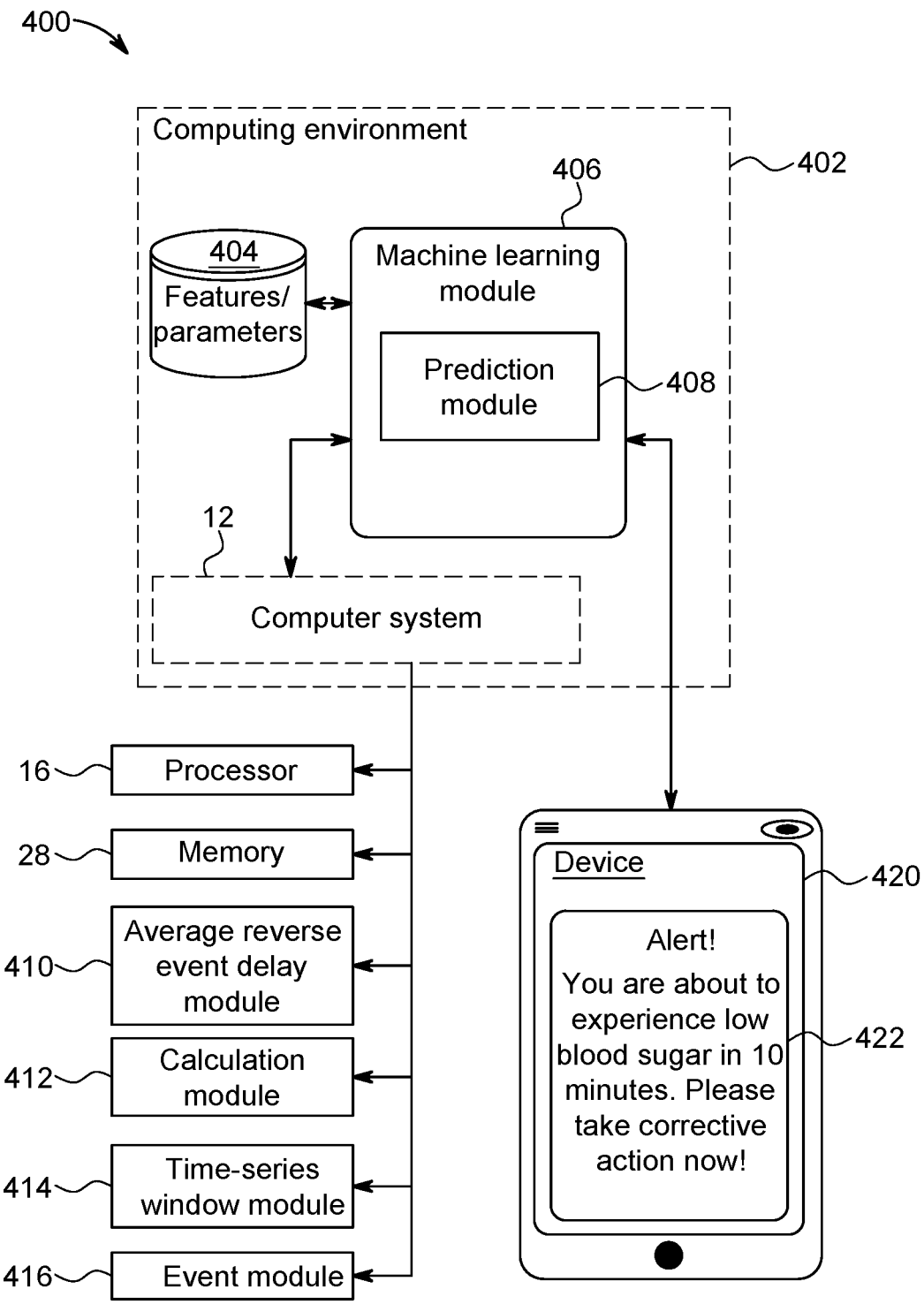
FIG. 4 is a diagram depicting various user hardware and computing components functioning in accordance with aspects of the present invention.

Turning now to FIG. 4, a block diagram depicting exemplary functional components 400 according to various mechanisms of the illustrated embodiments, is shown. FIG. 4 illustrates accurate temporal event predictive modeling and training of a machine-learning model in a computing environment, such as a computing environment 402, according to an example of the present technology. As will be seen, many of the functional blocks may also be considered "modules" of functionality, in the same descriptive sense as has been previously described in FIGS. 1-3. With the foregoing in mind, the module blocks 400 may also be incorporated into various hardware and software components of a system for accurate temporal event predictive modeling in accordance with the present invention. Many of the functional blocks 400 may execute as background processes on various components, either in distributed computing components, or on the user device, or elsewhere. Computer system/server 12 is again shown, incorporating processing unit 16 and memory 28 to perform various computational, data processing and other functionality in accordance with various aspects of the present invention.

The system 400 may include the computing environment 402 and a device 420, such as a desktop computer, laptop computer, tablet, smart phone, and/or another electronic device that may have one or more processors and memory. The device 420 and the computing environment 402 may each be associated with and/or in communication with each other, by one or more communication methods, such as a computing network. In one example, the device 420 may be controlled by an owner, customer, or patient associated with the computing environment 402. In another example, the device 420 may be completely independent from the owner, customer, or patient of the computing environment 402.

In one aspect, the computing environment 402 may provide virtualized computing services (i.e., virtualized computing, virtualized storage, virtualized networking, etc.) to devices 420. More specifically, the computing environment 402 may provide virtualized computing, virtualized storage, virtualized networking and other virtualized services that are executing on a hardware substrate.

As depicted in FIG. 4, the computing environment 402 may include a machine learning module 406, a features and/or parameters database 404 that is associated with a machine learning module 406. The computing environment 402 may also include a computer system 12, as depicted in FIG. 1. The computer system 12 may also include the average reverse event delay module 410, a calculation module 412, a time-series window module 414, and an event module 416 each associated with the machine learning module for training and learning one or more machine learning models and also for applying multiple combinations of features and/or parameters to the machine learning model that is being tested.

In one aspect, the machine learning module 406 may include a prediction module for predicting a future time-series event. For example, the computer system 12, using the time-series window module 414 and the event module 416, may define an event as a hypoglycemic event where the blood glucose level drops below a threshold in a time-series window after a bolus is administered by the patient.

In one aspect, the time-series window module 414 may use either a selected time period (e.g., a fixed period of time such as 2-4 hours) or use a time window that includes a selected number of events. An average event delay and an average reverse event delay may be calculated by the calculation module 412 in a time-series window and storing the average reverse event delay calculation in the average reverse event delay module 410. In one aspect, the calculation module 412 may calculate the event delay, average event delay, the average reverse event delay, and/or the time-series window according to mathematical operations or functions that may involve one or more mathematical operations (e.g., using addition, subtraction, division, multiplication, algebraic equations, calculus, standard deviations, means, averages, statistical modeling using statistical distributions, by finding minimums, maximums or similar thresholds for combined variables, etc.).

The average reverse event delay module 410 may define the average event delay as the average delay from a start of the time-series window after which the bolus event occurs. The average reverse event delay module 410 may also define the average reverse event delay as the average time from the end of the time-series window before which the event occurs.

One or more machine learning models or "classifiers" may be learned or trained by the machine learning module 406 using the average event delay and/or the prediction module 408 in addition to other features and/or parameters. The prediction module 408 may predict the hypoglycemic event in diabetic patients based on learned or trained classifiers.

The device 420 may include a graphical user interface (GUI) 422 enabled to display on the device 420 one or more user interface controls for a user to interact with the GUI 422. For example, the GUI 422 may display the predicted hypoglycemic event via an alert. For example, the predicted hypoglycemic event may be an alert that indicates or displays audibly and/or visually on the GUI 422 "ALERT! You are about to experience low blood sugar in 10 minutes. Please take corrective action now!"

The features/parameters 404 may be a combination of features/parameters and a recipe for processing features/parameters that may be applied to the same input data relating to testing, monitoring, and/or calculating various conditions or diagnostics of a condition of a patient. That is, different combinations of parameters may be selected and applied to the same input data for learning or training one or more machine learning models.

In one aspect, the accurate temporal event predictive modeling (or machine learning modeling), as described herein, may be performed using a wide variety of methods or combinations of methods, such as supervised learning, unsupervised learning, temporal difference learning, reinforcement learning and so forth. Some non-limiting examples of supervised learning which may be used with the present technology include AODE (averaged one-dependence estimators), artificial neural network, backpropagation, Bayesian statistics, naive bays classifier, Bayesian network, Bayesian knowledge base, case-based reasoning, decision trees, inductive logic programming, Gaussian process regression, gene expression programming, group method of data handling (GMDH), learning automata, learning vector quantization, minimum message length (decision trees, decision graphs, etc.), lazy learning, instance-based learning, nearest neighbor algorithm, analogical modeling, probably approximately correct (PAC) learning, ripple down rules, a knowledge acquisition methodology, symbolic machine learning algorithms, sub symbolic machine learning algorithms, support vector machines, random forests, ensembles of classifiers, bootstrap aggregating (bagging), boosting (meta-algorithm), ordinal classification, regression analysis, information fuzzy networks (IFN), statistical classification, linear classifiers, fisher's linear discriminant, logistic regression, perceptron, support vector machines, quadratic classifiers, k-nearest neighbor, hidden Markov models and boosting. Some non-limiting examples of unsupervised learning which may be used with the present technology include artificial neural network, data clustering, expectation-maximization, self-organizing map, radial basis function network, vector quantization, generative topographic map, information bottleneck method, IBSEAD (distributed autonomous entity systems based interaction), association rule learning, apriori algorithm, eclat algorithm, FP-growth algorithm, hierarchical clustering, single-linkage clustering, conceptual clustering, partitional clustering, k-means algorithm, fuzzy clustering, and reinforcement learning. Some non-limiting example of temporal difference learning may include Q-learning and learning automata. Specific details regarding any of the examples of supervised, unsupervised, temporal difference or other machine learning described in this paragraph are known and are considered to be within the scope of this disclosure. Also, when deploying one or more machine learning models, a computing device may be first tested in a controlled environment before being deployed in a public setting. Also even when deployed in a public environement (e.g., external to the controlled, testing environment), the computing devices may be monitored for compliance.

Figure 5:
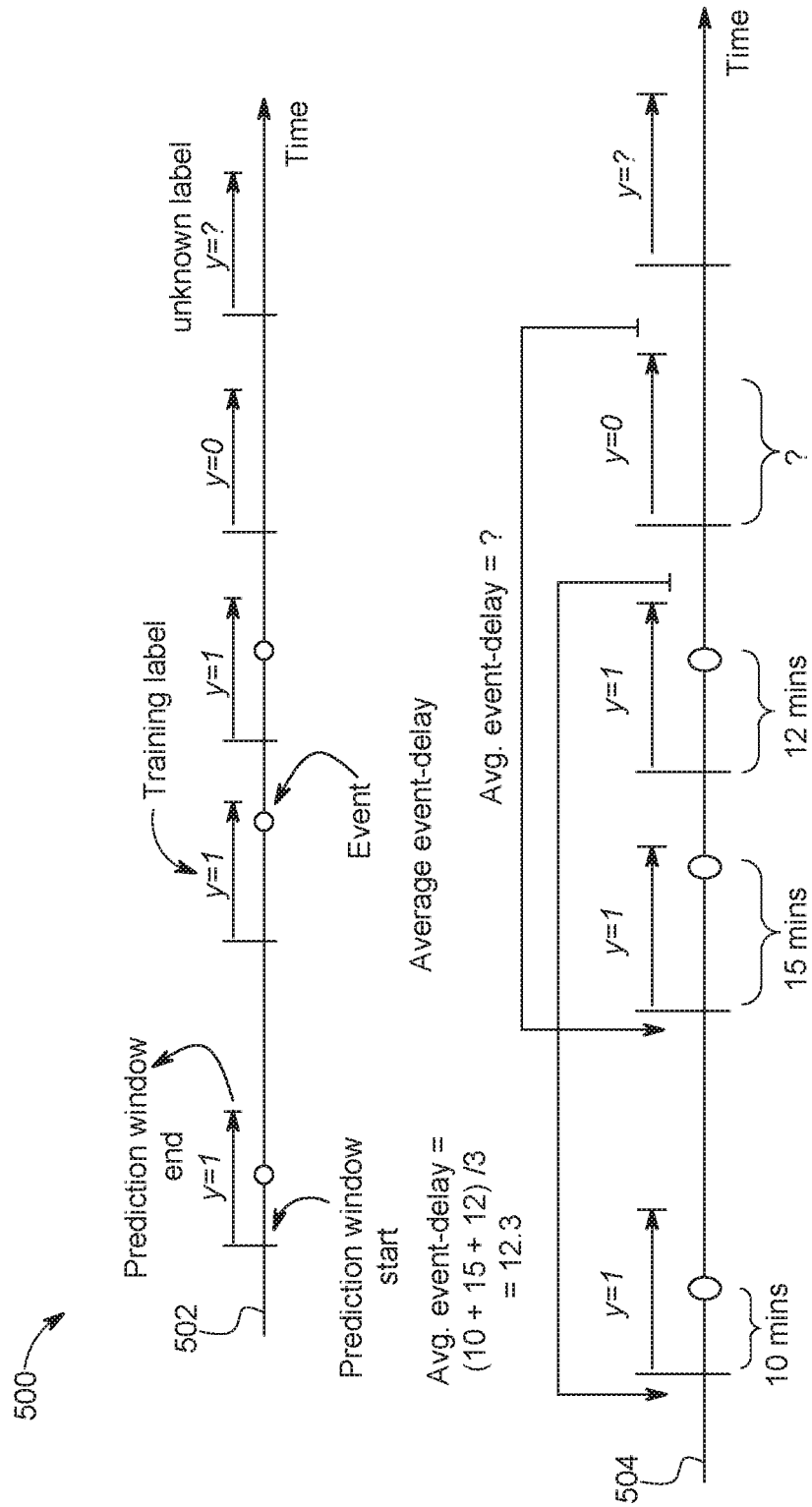
FIG. 5 is a diagram depicting a time-window with average event delay of event in accordance with aspects of the present invention.

Turning now to FIG. 5, an exemplary time-window with average event delay of event 500 is depicted illustrating time windows 502 and 504. Time windows 502 and 504 are identically illustrated with the time windows more clearly depicting an average event delay. Time window 502 is used to depict the starting of each prediction window (start time) and each event. Labels "Y" denote whether an event, such as a hypoglycemic event, has occurred or not in a particular time window, such as time windows 502 or 504. That is, label "Y" may equal a first value such as, for example, one ("1"), and the first value may mean or indicate an event (e.g., hypoglycemic event) has occurred. In an additional example, label "Y" may equal a second value such as, for example, zero ("0"), and may mean or indicate that an event (e.g., hypoglycemic event) may not have occurred. In one aspect, the variable "Y" indicates a training label or feature/parameter. Each event in each time window is indicated as a solid circle on the time windows 502 and 504. Using the training windows and event occurrences, the machine learning model should derive accurate feature(s) for predicting whether the event will occur in an unknown/testing time-window. The start of the time-window may be associated with a certain observed action or event, such as, for example, administration of a bolus. For example, for predicting a hypoglycemia event, the time window may start at a bolus event. At this point, the machine learning model predict attempts to determine whether a hypoglycemic event may occur within a time window, such as 4 hours, from the bolus event. In one aspect, one or more of the features/parameters should be correlated with a training label, such as label "y". The feature values may be finite and continuous. The continuous features may be helpful to classifiers (e.g., machine learning model) such as, for example a random forest for finding optimal split points.

As depicted in time window 504, one or more of the features/parameters (e.g., predictor) may be the average event delay for predicting the time-series event (e.g., the hypoglycemia event). The average event delay may be defined as the average delay from the start of the window after which the event occurs.

As depicted, in a first time window, a first event (e.g., hypoglycemia event) occurs 10 minutes from the bolus in the first time window. In a second time window, a second event (e.g., a second hypoglycemia event) occurs 15 minutes from the bolus in the second time window. In a third time window, a third event (e.g., a third hypoglycemia event) occurs 12 minutes from the bolus in the third time window. However, in a fourth time window, a future event is unknown. The average event delay may then be calculated by adding each of the determined time values of the event delays of each event in each past time window and dividing the total sum by the 3 windows such as, for example, (10+15+12)/3 equals 12.3. However, for cases where label y equals 0 (e.g., y=0), or when the time-series event does not occur (e.g., the event is still a future event) in the time window, the event delay could be infinity and/or not available (N/A). Therefore, the values of average event delay may not be finite and thus would be impossible to determine or predict the future time series event (e.g., the future hypoglycemia event that has yet to occur).

Figure 6:
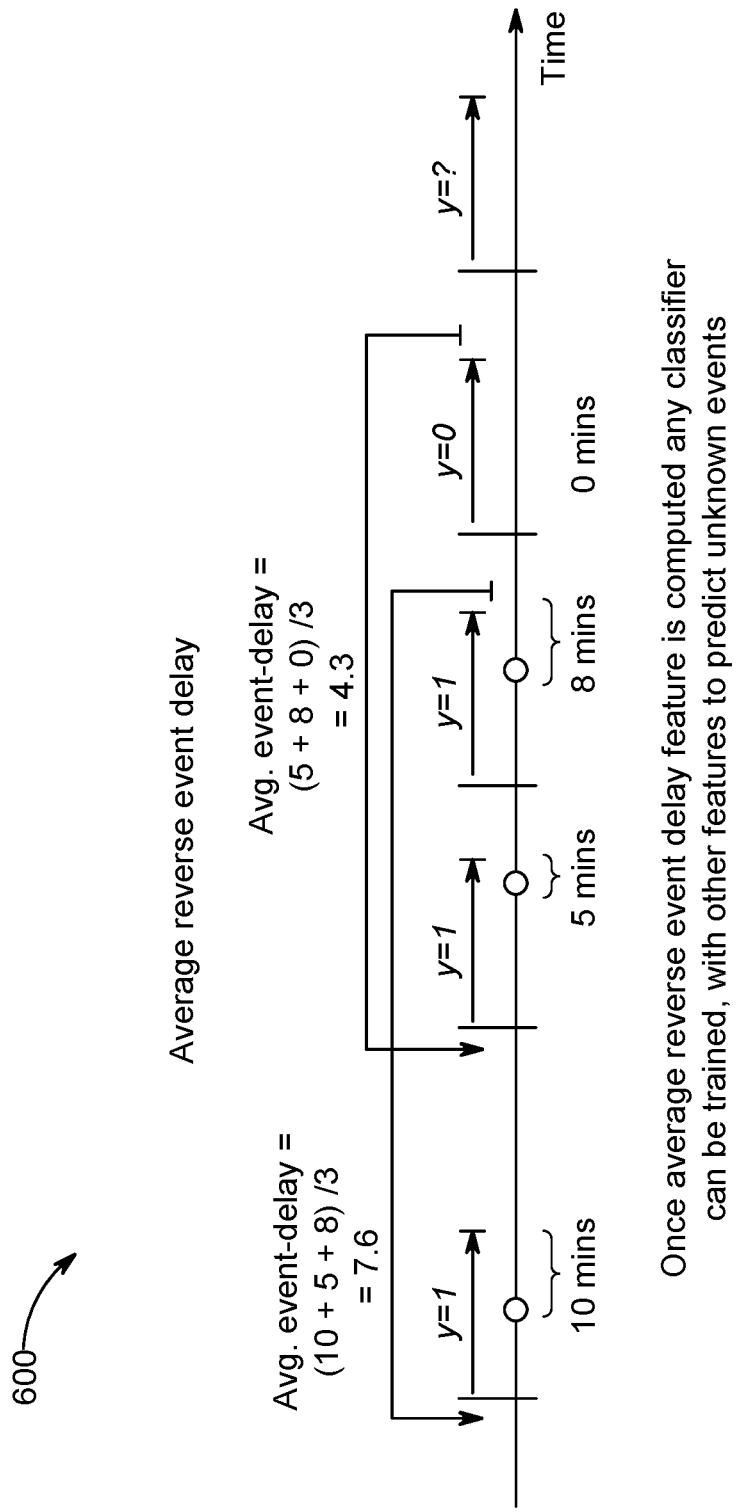
FIG. 6 is a diagram depicting a time-window with average reverse event delay for accurate temporal event predictive modeling in accordance with aspects of the present invention.

Accordingly, FIG. 6 provides a solution to the challenge illustrated in FIG. 5 where y equals 0 (e.g., y=0), or when the time-series event does not occur (is still a future event) in the time window, the event delay could be infinity and/or not available (N/A). That is, FIG. 6 is a diagram depicting a time-window with average reverse event delay for accurate temporal event predictive modeling 600. In contrast to the average event delay where the event delay is computed from the start of a time window up until the occurrence of the event, the average reverse event delay reverses the computation and calculates the event delay from the end of the time window backwards (or reverse) to the event. In this way, a zero value may now be associated with a non-event, such as in the fourth time window as depicted in both FIGS. 5 and 6.

In one aspect, the average reverse event delay is defined as the average time from the end of the window before which the event occurs. The average reverse event delay feature has an advantage that its value can be set to 0 when y=0 and its value is greater than zero (e.g., >0) for when y is equal to one (y=1). Intuitively it captures similar characteristics as the average event delay. However, the main difference is that in rare class problems (where y=0 is more prevalent) the average event delay cannot be computed for a large number of cases. Thus, the average reverse event delay corrects the classification problem of class imbalance such as when a minority class is important. That is, there may be several instances in important machine learning problems where there naturally exists a class imbalance. For example, assume a user is interested in predicting whether a patient will experience an event, such as death resulting from a hypoglycemic event. In reality, a majority of patients will not experience death resulting from a hypoglycemic event. Therefore, in this scenario, there is a large class imbalance between the majority (e.g., greater than 75%) of patients that will not suffer death resulting from a hypoglycemic event as compared to the minority (e.g., less than 25%) of patients that may suffer death resulting from a hypoglycemic event. Similarly, patients rarely have hypoglycemia. This is because the hypoglycemic event may be life-threatening and most trained patients react quickly as they start feeling dizzy. Therefore, in this example the dataset naturally has class imbalance since the boluses that lead to hypoglycemia may be about 8-9%. Once the average reverse event delay feature is computed, any classifier (e.g., machine learning model) may be trained along with one or more other features/parameters that may be used to predict unknown labels or the time-series event.

In operation, as illustrated in FIG. 6, in a first time window a first event (e.g., hypoglycemia event) occurs 10 minutes from the bolus in the first time window. In a second time window, a second event (e.g., a second hypoglycemia event) occurs 5 minutes from the bolus in the second time window. In a third time window, a third event (e.g., a third hypoglycemia event) occurs 8 minutes from the bolus in the third time window. However, in a fourth time window, a future event is unknown. One or more average reverse event delays may be then calculated by adding each of the determined time values of the event delays of each event in each past time window and then dividing by a total sum of time windows that are being analyzed. For example, a first average reverse event delay may be calculated as (10+5+8) divided by 3 with 3 being the total sum by the 3 windows. The calculation yields an average reverse event delay as equal to 7.6. A second average reverse event delay may be calculated as (5+8+0) divided by 3 with 3 being the total sum by the 3 windows and zero being set as the non-event of the fourth window. The calculation yields an average reverse event delay as equal to 4.3.

Figure 7B:
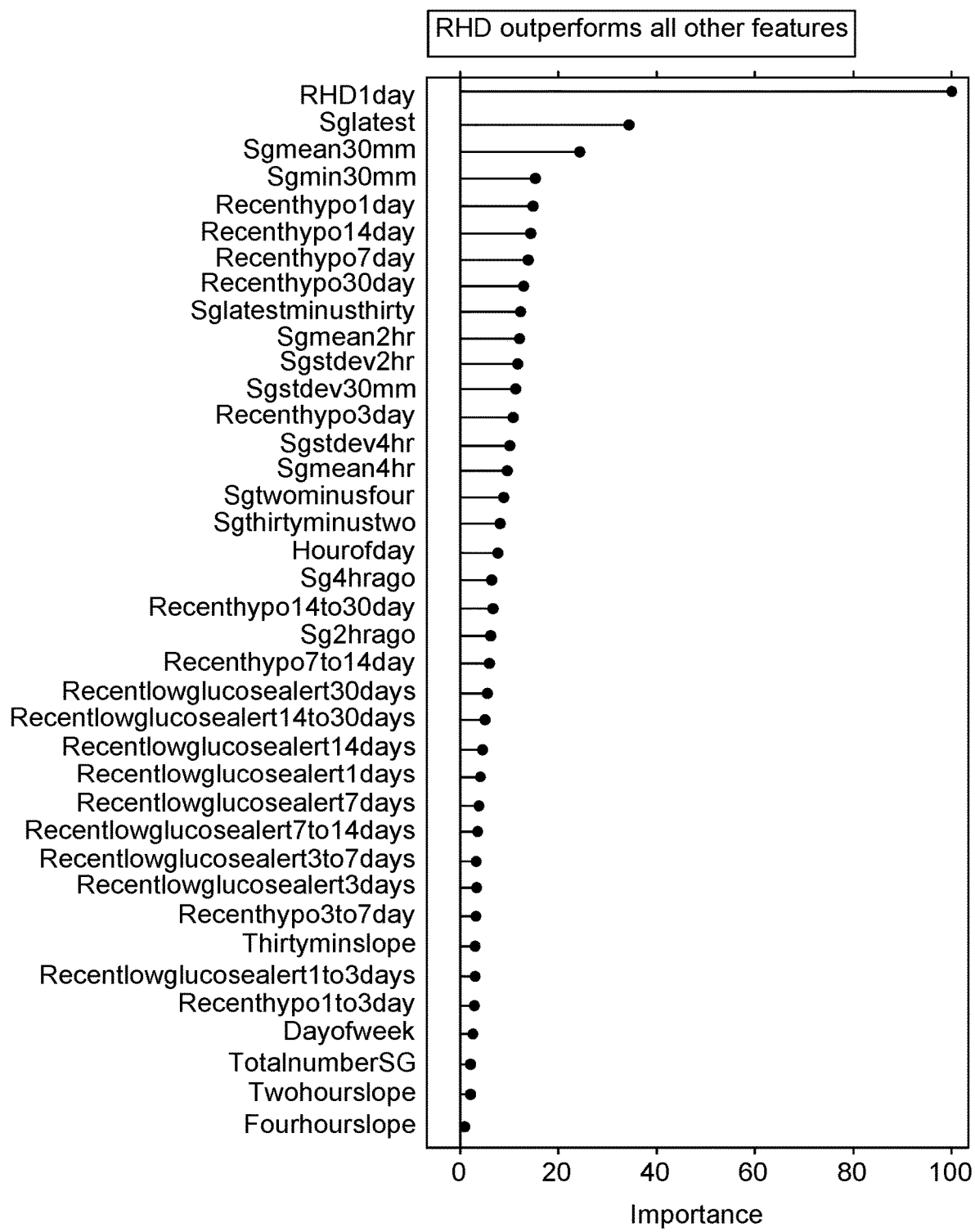

Turning now to FIGS. 7A-B is a diagram of prediction results 700 using average reverse event delay in predictive modeling. As illustrated, the average reverse event delay embodiment as described herein is applied to a hypoglycemia prediction model. In the first column, a list of group of patients are identified according to a group ID. The second, third, and fourth column are time-series windows of 2 hours (hr), 3 hours (hr), and 4 hours (hr), respectively. Within each time-series window, 10,000 (10K) patients are each tested for predicting a hypoglycemia event. As illustrated, the results of hypoglycemia prediction are displayed for both using a reverse hypo delay (RHD), which may be equivalent to the average reverse event delay, and using one or more features, and also a prediction model with one or more features that do not include the RHD. A minimum (min), a maximum (max), and a mean of the entire set of groups (e.g., groups 1-10) are illustrated. As illustrated, the use of the average reverse event delay in the prediction model to predict the hypoglycemia event is more accurate and reliable than performing the prediction model without the average reverse event delay or RHD. Moreover, even when using the one or more additional features, the RHD outperforms all other features.

With the foregoing functional components in view, consider some of the various aspects of the illustrated embodiments. In one aspect, the illustrative embodiments solve a classification problem of predicting time-series events using reverse average event delay and average event delay where classification creates an imbalance of classes where a minority class designed as important or high priority but unable to be classified as such. A classifier ("prediction model") may be trained or learned using the average reverse event delay and/or the average event delay in addition to other features. A label for a test data point may be determined by labeling the test data point using the classifier learned using the average reverse event delay and/or the average event delay in addition to other pre-existing features.

In an additional aspect, the illustrative embodiments may be used for predicting hypoglycemic events in Type 1 and Type II Diabetes Patients. A hypoglycemia event may be defined as a blood glucose level dropping below a threshold in a 2-4 hour window after a bolus is administered by the patient. A reverse hypo delay (RHD which may be equivalent to the average reverse event delay) may be computed using the 2-4 window and a plurality of features are derived in a time window prior to the bolus event. Each of the features (including the RHD) may be derived in windows ranging from a few minutes to a few months. A bolus event may have two labels: hypoglycemic (HYPO) or non-hypoglycemic (NON-HYPO), depending on whether a hypoglycemic event has occurred or not in the 2-4 hour window that may be defined as a fixed time period of a window that may include one or more hypoglycemic (HYPO) or non-hypoglycemic (NON-HYPO) events. The prediction of a hypoglycemic event can be in the form of probability distribution over the set of labels such as, for example, the prediction for a test point may be 0.7 for the HYPO event or 0.3 for a NON-HYPO event.

Furthermore, one or more classifiers (known as weak learners) may be learned after grouping the features using an unsupervised operation. That is, once all the features are computed (including the average event delay) these features may be grouped together using an unsupervised operation such as, for example, data clustering. Cluster analysis or clustering may be the task of grouping a set of objects in such a way that objects in the same group (called a cluster) are more similar (in some sense or another) to each other than to those in other groups (clusters). After clustering, each group may contain similar types of events. Now for each group, a machine learning model may be learned or trained to predict an event such as, for example, hypoglycemia. This improves prediction accuracy because by clustering the features, localized groups of data points may be formed. The machine learning model may be trained per-cluster (or per group), rather than just training one machine learning model for all data to enable increased prediction accuracy.

The weak learners may be learned or trained to detect the various sub-types of one or more minority classes, where such sub-types may be obtained by a clustering process. In one aspect, the sub-types may be detected by clustering the features. The sub-types are learned from the data using unsupervised methods (as described above). A minority class may be partitioned into groups/clusters using an average reverse event delay. A prediction for a test point may be obtained by combining the predictions from the K classifiers in the ensemble point. A feature vector may be computed around a bolus event that can be computed based on different data sources and labeled as being hypoglycemic (HYPO) or non-hypoglycemic (NON-HYPO) using pre-established criteria. For example, the pre-established criteria may be data related to an event such as, for example hypoglycemia defined as the blood glucose dropping below 70 mg/dl for about 10 minutes within a time window (e.g., 4 hr, 3 hr, or 2 hr) after a patient injects himself/herself with a bolus. Therefore, if the blood glucose level drops below 70 mg/dl during the time window after the bolus, the event may be "marked" (e.g., an indication) as HYPO, otherwise it may be marked as NON-HYPO. That is, past data may be used to find out which boluses are HYPO or NON-HYPO and then one or more features may be extracted from the data and a machine learning algorithm may be trained to predict whether a bolus will be HYPO or NON-HYPO.

The machine learning model may be built using either a cost minimization technique such as, for example, a gradient descent or other techniques using the Gini index. One or more individual models in the ensemble method can be learned using a variety of classification algorithms like decision forests, support vector machine (SVM), logistic regression, etc. The misclassification cost is measured using the area-under-curve of a receiver operating characteristic (ROC) where the HYPO is class and is treated as positive. Other measures such as positive predictive values (PPV) may also be used to measure performance.

Figure 8:
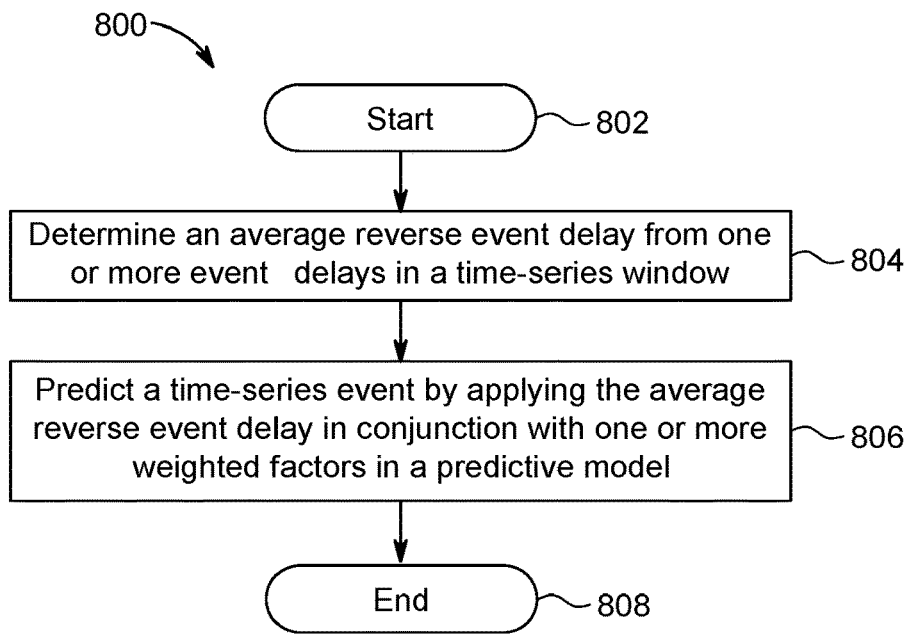
FIG. 8 is a flowchart diagram of an exemplary method for accurate temporal event predictive modeling by a processor, in which various aspects of the present invention may be realized.

Turning now to FIG. 8, a method 800 for accurate temporal event predictive modeling by a processor is depicted, in which various aspects of the illustrated embodiments may be implemented. The functionality 800 may be implemented as a method executed as instructions on a machine, where the instructions are included on at least one computer readable medium or one non-transitory machine-readable storage medium. The functionality 800 may start in block 802. An average reverse event delay may be determined from one or more event delays in a time-series window, as in block 804. A time-series event may be predicted by applying the average reverse event delay in conjunction with one or more weighted factors in a predictive model, as in block 806. The functionality 800 may end in block 808.

Figure 9:
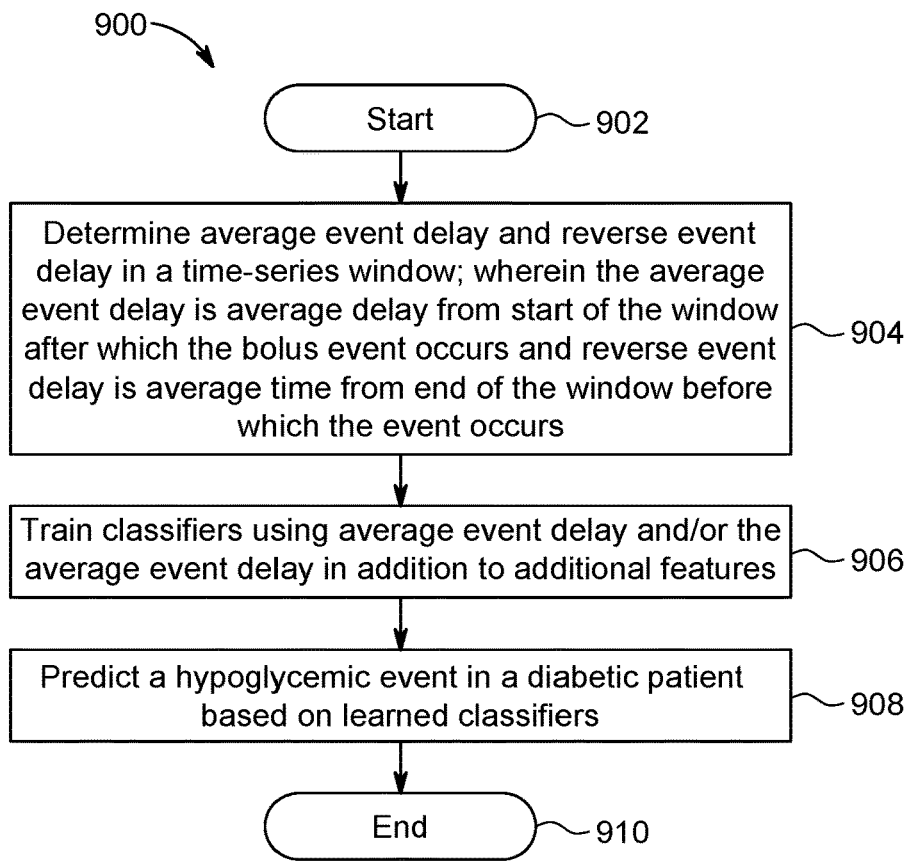
FIG. 9 is an additional flowchart diagram of an additional exemplary method for accurate temporal event predictive modeling by a processor, here again in which various aspects of the present invention may be realized.

FIG. 9 is an additional method 900 for accurate temporal event predictive modeling by a processor, in which various aspects of the illustrated embodiments may be implemented. The functionality 900 may be implemented as a method executed as instructions on a machine, where the instructions are included on at least one computer readable medium or one non-transitory machine-readable storage medium. The functionality 900 may start in block 902. An average event delay and reverse event delay may be calculated or determined in a time-series window, as in block 904. The average event delay is average delay from start of the window after which the bolus event occurs and reverse event delay is average time from end of the window before which the event occurs. One or more classifiers may be trained (learned) using the average event delay and/or the average event delay in addition to additional features, as in block 906. A hypoglycemic event in a diabetic patient may be predicted based on learned classifiers, as in block 908. The functionality 900 may end in block 910.

In one aspect, in conjunction with and/or as part of at least one block of FIG. 8 or 9, the operations of methods 800 and/or 900 may include each of the following. The operations of method 900 may include identifying the time-series window as a selected time period or one or more events. The event delay may be identified in the time-series window as time delay starting at a beginning of the time-series window until occurrence of an event. The average event delay may be identified as an average time delay from start of the time-series window until occurrence of an event. The average reverse event delay may be identified as an average time period of the one or more event delays starting from an end of the time-series window prior to occurrence of the time-series event.

The operations of method 900 may include setting the time-series event as zero for determining the average reverse event delay. The operations of method 900 may include training the predictive model using the average reverse event delay and an average event delay, wherein the average event delay is an average time delay from start of the time-series window until occurrence of an event and the average reverse event delay is an average time period of the one or more event delays starting from an end of the time-series window prior to occurrence of the time-series event and/or predicting a hypoglycemic event, as the time-series event, of a patient based on the learned predictive model.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowcharts and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowcharts and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowcharts and/or block diagram block or blocks.

The flowcharts and block diagrams in the Figures illustrate the architecture, functionality, and operation of possible implementations of systems, methods, and computer program products according to various embodiments of the present invention. In this regard, each block in the flowcharts or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustrations, and combinations of blocks in the block diagrams and/or flowchart illustrations, can be implemented by special purpose hardware-based systems that perform the specified functions or acts or carry out combinations of special purpose hardware and computer instructions.

The invention claimed is:

1. A method for accurate temporal event predictive modeling by a processor, comprising:
   monitoring medical data of a patient over a plurality of time-series windows;
   detecting, based on the monitoring, one or more time-series events for the patient, each time-series event occurring within a time-series window, each time-series event being associated with a medical condition of the patient;
   determining a reverse event delay for each of the plurality of time-series windows,
   wherein the reverse event delay is an amount of time between the end of the time-series window and an occurrence of a corresponding time-series event;
   setting, in response to determining a time-series event did not occur in a particular time-series window, a reverse event delay associated with the particular time-series window as zero for determining the average reverse event delay;
   determining an average reverse event delay from the plurality of reverse event delays;
   training a predictive model using the average reverse event delay and an average event delay, wherein the average event delay is an average time delay from the start of the time-series window until occurrence of a time-series event; and
   predicting a future time-series event for the patient by applying the average reverse event delay in conjunction with one or more weighted factors in the predictive model.

2. The method of claim 1, further including identifying the time-series window as a selected time period or one or more events.

3. The method of claim 1, further including identifying an event delay in the time-series window as a time delay starting at a beginning of the time-series window until occurrence of an event.

4. The method of claim 1, further including:
   predicting a hypoglycemic event, as the time-series event, of the patient based on the learned predictive model.

5. A system for accurate temporal event predictive modeling, comprising:
   a processor configured to perform a method comprising:
   monitoring medical data of a patient over a plurality of time-series windows;
   detecting, based on the monitoring, one or more time-series events for the patient, each time-series event occurring within a time-series window, each time-series event being associated with a medical condition of the patient;
   determining a reverse event delay for each of the plurality of time-series windows,
   wherein the reverse event delay is an amount of time between the end of the time-series window and an occurrence of a corresponding time-series event;
   setting, in response to determining a time-series event did not occur in a particular time-series window, a reverse event delay associated with the particular time-series window as zero for determining the average reverse event delay;
   determining an average reverse event delay from the plurality of reverse event delays;
   training a predictive model using the average reverse event delay and an average event delay, wherein the average event delay is an average time delay from the start of the time-series window until occurrence of a time-series event; and
   predicting a future time-series event for the patient by applying the average reverse event delay in conjunction with one or more weighted factors in the predictive model.

6. The system of claim 5, wherein the method further comprises identifying the time-series window as a selected time period or one or more events.

7. The system of claim 5, wherein the method further comprises identifying an event delay in the time-series window as a time delay starting at a beginning of the time-series window until occurrence of an event.

8. The system of claim 5, wherein the method further comprises:
   predicting a hypoglycemic event, as the time-series event, of the patient based on the learned predictive model.

9. A computer program product for accurate temporal event predictive modeling by a processor, the computer program product comprising a computer readable storage medium having program instructions embodied therewith, the program instructions executable by processor to cause the processor to perform a method comprising:
   analyzing medical data for a patient, wherein the medical data includes data for a plurality of time-series windows;
   identifying, based on the analyzing, one or more time-series events for the patient, each of the one or more time-series events occurring within a time-series window;
   determining a reverse event delay for each of the time-series windows, wherein the reverse event delay for a respective time-series window is an amount of time between an occurrence of a time-series event in the respective time-series window and the end of the respective time-series window;
   setting, in response to determining a time-series event did not occur in a particular time-series window, a reverse event delay associated with the particular time-series window as zero for determining the average reverse event delay;
   determining an average reverse event delay from the plurality of reverse event delays;
   training a predictive model using the average reverse event delay and an average event delay, wherein the average event delay is an average time delay from the start of the time-series window until occurrence of a time-series event; and
   predicting a future time-series event for the patient by applying the average reverse event delay in conjunction with one or more weighted factors in the predictive model.

10. The computer program product of claim 9, wherein the method further comprises identifying each of the plurality of time-series windows as a period between an occurrence of two or more events.

11. The computer program product of claim 9, wherein the method further comprises identifying:
an event delay in each of the plurality of time-series windows, wherein the event delay for each respective time-series window is the time delay starting at a beginning of the respective time-series window until occurrence of a time-series event in the respective time-series window.

12. The computer program product of claim 9, wherein the method further comprises:
predicting a hypoglycemic event, as the time-series event, of the patient based on the learned predictive model.

13. The computer program product of claim 9, wherein identifying the reverse event delay for each of the plurality of time-series windows comprises:
identifying a first time-series window, wherein the first time-series window is a window that starts at an occurrence of a first event and ends a predetermined amount of time later;
determining whether a first time-series event occurs within the first time-series window;
if the first time-series event occurs within the first time-series window, calculating a first reverse event delay of the plurality of reverse event delays as an amount of time between an occurrence of the first time-series event and the end of the first time-series window; and
if the first time-series event does not occur within the first time-series window, setting the first reverse event delay as zero.

14. The computer program product of claim 13, wherein the plurality of reverse event delays further includes a second reverse event delay associated with a second time-series window that starts at an occurrence of a second event, and wherein determining the average reverse event delay from the plurality of reverse event delays comprises determining an average of the first and second reverse event delays.

15. The computer program product of claim 14, wherein the first event is a first bolus event and the second event is a second bolus event, wherein the first time-series event is a hypoglycemic event, and wherein determining whether the first time-series event occurs within the first time-series window includes:
determining whether a blood glucose level of the patient drops below 70 mg/dl during the first time-series window;
if the blood glucose level of the patient drops below 70 mg/dl during the first time-series window, determining that the first time-series event occurred; and
if the blood glucose level of the patient does not drop below 70 mg/dl during the first time-series window, determining that the first time-series event did not occur.

* * * * *